(12) United States Patent
Coroneo

(10) Patent No.: US 8,128,588 B2
(45) Date of Patent: Mar. 6, 2012

(54) OCULAR PRESSURE REGULATION

(75) Inventor: Minas Theodore Coroneo, Randwick (AU)

(73) Assignee: Transcend Medical, Inc., Menlo Park, CA (US)

( * ) Notice: Subject to any disclaimer, the term of this patent is extended or adjusted under 35 U.S.C. 154(b) by 0 days.

(21) Appl. No.: 11/615,642

(22) Filed: Dec. 22, 2006

(65) Prior Publication Data
US 2007/0106236 A1 May 10, 2007

Related U.S. Application Data

(63) Continuation of application No. 10/712,277, filed on Nov. 14, 2003, now Pat. No. 7,291,125.

(51) Int. Cl.
*A61M 5/00* (2006.01)
*A61M 1/00* (2006.01)
*A61F 11/00* (2006.01)

(52) U.S. Cl. .............. 604/8; 604/9; 604/27; 606/108

(58) Field of Classification Search .......... 604/7–10, 604/93, 294, 48, 117, 27–31, 93.01, 289–291, 604/503, 505; 128/347–348; 606/107–109, 606/167, 170
See application file for complete search history.

(56) References Cited

U.S. PATENT DOCUMENTS

| | | |
|---|---|---|
| 3,767,759 A | 10/1973 | Wichterle |
| 3,788,327 A * | 1/1974 | Donowitz et al. ............. 604/247 |
| 3,915,172 A | 10/1975 | Wichterle et al. |
| 4,037,604 A | 7/1977 | Newkirk |
| 4,402,681 A * | 9/1983 | Haas et al. .................. 604/9 |
| 4,457,757 A | 7/1984 | Molteno .................. 604/294 |
| 4,521,210 A | 6/1985 | Wong .................. 604/8 |
| 4,554,918 A | 11/1985 | White .................. 604/10 |
| 4,604,087 A | 8/1986 | Joseph .................. 604/9 |
| 4,634,418 A | 1/1987 | Binder .................. 604/8 |
| 4,722,724 A | 2/1988 | Schocket |

(Continued)

FOREIGN PATENT DOCUMENTS

EP 0228185 7/1987

(Continued)

OTHER PUBLICATIONS

Classen, L., et al., "A histopathologic and immunohistorchemical analysis of the filtration bleb after unsuccessful glaucoma seton implantation," American Journal of Opthamology, 122:205-212, (1996).

(Continued)

*Primary Examiner* — Tatyana Zalukaeva
*Assistant Examiner* — Philip R Wiest
(74) *Attorney, Agent, or Firm* — Fred C. Hernandez; Mintz, Levin, Cohn, Ferris, Glovsky and Popeo, P.C.

(57) ABSTRACT

This invention comprises a flexible ocular device for implantation into the eye formed of a biocompatible elastomeric material, foldable to a diameter of 1.5 mm or less, comprising a fluid drainage tube having at one end a foldable plate adapted to locate the device on the inner surface of the sclera in a suprachoroidal space formed by cyclodialysis, said drainage tube opening onto the disc at one end and opening to the anterior chamber when implanted into the eye at its other end, so as to provide aqueous pressure regulation. Also provided are methods for the treatment of glaucoma utilizing the flexible ocular device, and an ocular pressure spike shunt.

38 Claims, 4 Drawing Sheets

U.S. PATENT DOCUMENTS

| | | | |
|---|---|---|---|
| 4,750,901 A | 6/1988 | Molteno | |
| 4,787,885 A | 11/1988 | Binder | 604/8 |
| 4,826,478 A | 5/1989 | Schocket | 604/8 |
| 4,846,172 A | 7/1989 | Berlin | |
| 4,863,457 A | 9/1989 | Lee | |
| 4,886,488 A | 12/1989 | White | 604/9 |
| 4,900,300 A | 2/1990 | Lee | |
| 4,946,436 A | 8/1990 | Smith | |
| 4,968,296 A | 11/1990 | Ritch et al. | 604/8 |
| 5,041,081 A | 8/1991 | Odrich | 604/9 |
| 5,071,408 A | 12/1991 | Ahmed | 606/108 |
| 5,073,163 A | 12/1991 | Lippman | |
| 5,092,837 A | 3/1992 | Ritch et al. | 604/8 |
| 5,127,901 A | 7/1992 | Odrich | 604/9 |
| 5,171,213 A | 12/1992 | Price, Jr. | 604/9 |
| 5,178,604 A | 1/1993 | Baerveldt et al. | 604/8 |
| 5,180,362 A | 1/1993 | Worst | 604/8 |
| 5,300,020 A | 4/1994 | L'Esperance, Jr. | 604/9 |
| 5,338,291 A | 8/1994 | Speckman et al. | 604/9 |
| 5,342,370 A | 8/1994 | Simon et al. | 606/107 |
| 5,346,464 A | 9/1994 | Camras | 604/9 |
| 5,370,607 A | 12/1994 | Memmen | 604/8 |
| 5,372,577 A | 12/1994 | Ungerleider | |
| 5,397,300 A | 3/1995 | Baerveldt et al. | 604/8 |
| 5,433,701 A | 7/1995 | Rubinstein | 604/8 |
| 5,443,505 A * | 8/1995 | Wong et al. | 623/4.1 |
| 5,454,746 A | 10/1995 | Guegan et al. | 446/72 |
| 5,476,445 A | 12/1995 | Baerveldt et al. | 604/8 |
| 5,558,629 A * | 9/1996 | Baerveldt et al. | 604/8 |
| 5,558,630 A | 9/1996 | Fisher | |
| 5,601,094 A * | 2/1997 | Reiss | 128/899 |
| 5,626,558 A | 5/1997 | Suson | 604/8 |
| 5,626,559 A | 5/1997 | Solomon | |
| 5,651,782 A | 7/1997 | Simon et al. | 606/1 |
| 5,676,944 A | 10/1997 | Alvarado et al. | 424/93.71 |
| 5,702,414 A | 12/1997 | Richter et al. | 606/166 |
| 5,704,907 A | 1/1998 | Nordquist et al. | 604/8 |
| 5,713,844 A | 2/1998 | Peyman | |
| 5,741,292 A | 4/1998 | Mendius | 606/191 |
| 5,743,868 A | 4/1998 | Brown et al. | 604/8 |
| 5,752,928 A | 5/1998 | De Roulhac et al. | |
| 5,807,302 A | 9/1998 | Wandel | |
| 5,868,697 A | 2/1999 | Richter et al. | 604/8 |
| 5,882,327 A | 3/1999 | Jacob | 604/8 |
| 5,893,837 A | 4/1999 | Eagles et al. | 604/9 |
| 5,968,058 A | 10/1999 | Richter et al. | 606/166 |
| 6,007,510 A | 12/1999 | Nigam | 604/8 |
| 6,007,511 A * | 12/1999 | Prywes | 604/9 |
| 6,019,786 A | 2/2000 | Thompson | |
| 6,050,970 A | 4/2000 | Baerveldt | 604/28 |
| 6,077,299 A | 6/2000 | Adelberg et al. | 623/24 |
| 6,102,045 A | 8/2000 | Nordquist et al. | 128/898 |
| 6,142,969 A | 11/2000 | Nigam | 604/8 |
| 6,186,974 B1 | 2/2001 | Allan et al. | 604/30 |
| 6,203,513 B1 | 3/2001 | Yaron et al. | 604/9 |
| 6,221,078 B1 | 4/2001 | Bylsma | 606/107 |
| 6,251,090 B1 | 6/2001 | Avery et al. | 604/9 |
| 6,261,256 B1 | 7/2001 | Ahmed | 604/9 |
| 6,264,668 B1 | 7/2001 | Prywes | 606/167 |
| 6,331,313 B1 | 12/2001 | Wong et al. | |
| 6,375,642 B1 | 4/2002 | Grieshaber et al. | |
| 6,383,219 B1 | 5/2002 | Telandro et al. | |
| 6,450,984 B1 | 9/2002 | Lynch et al. | 604/8 |
| 6,464,724 B1 | 10/2002 | Lynch et al. | |
| 6,468,283 B1 | 10/2002 | Richter et al. | 606/108 |
| 6,471,666 B1 | 10/2002 | Odrich | 604/8 |
| 6,471,777 B1 | 10/2002 | Kobayashi et al. | 118/500 |
| 6,508,779 B1 | 1/2003 | Suson | 604/8 |
| 6,510,600 B2 | 1/2003 | Yaron et al. | 29/428 |
| 6,524,275 B1 | 2/2003 | Lynch et al. | 604/96.01 |
| 6,533,768 B1 | 3/2003 | Hill | 604/521 |
| 6,537,568 B2 | 3/2003 | Olejnik et al. | |
| 6,544,208 B2 | 4/2003 | Ethier et al. | 604/8 |
| 6,544,249 B1 | 4/2003 | Yu et al. | 604/521 |
| 6,558,342 B1 | 5/2003 | Yaron et al. | 604/9 |
| 6,589,203 B1 | 7/2003 | Mitrev | 604/27 |
| 6,595,945 B2 | 7/2003 | Brown | 604/8 |
| 6,626,858 B2 | 9/2003 | Lynch et al. | 604/8 |
| 6,638,239 B1 | 10/2003 | Bergheim et al. | 604/27 |
| 6,666,841 B2 | 12/2003 | Gharib et al. | 604/8 |
| 6,676,607 B2 | 1/2004 | De Juan, Jr. et al. | |
| 6,699,210 B2 | 3/2004 | Williams et al. | 604/8 |
| 6,699,211 B2 | 3/2004 | Savage | 604/9 |
| 6,719,750 B2 | 4/2004 | Varner et al. | 604/289 |
| 6,726,664 B2 | 4/2004 | Yaron et al. | 604/265 |
| 6,730,056 B1 | 5/2004 | Ghaem et al. | 604/9 |
| 6,736,791 B1 | 5/2004 | Tu et al. | 604/8 |
| 6,783,544 B2 | 7/2004 | Burns et al. | 604/8 |
| 6,780,164 B2 | 8/2004 | Bergheim et al. | 604/8 |
| 6,827,699 B2 | 12/2004 | Lynch et al. | 604/8 |
| 6,827,700 B2 | 12/2004 | Lynch et al. | 604/8 |
| 6,955,656 B2 | 12/2004 | Lynch et al. | 604/8 |
| 6,881,197 B1 | 4/2005 | Nigam | 604/8 |
| 6,881,198 B2 | 4/2005 | Brown | 604/8 |
| 6,939,298 B2 | 9/2005 | Brown et al. | |
| 6,962,573 B1 | 11/2005 | Wilcox | 604/9 |
| 6,966,888 B2 | 11/2005 | Cullen et al. | |
| 6,969,384 B2 | 11/2005 | De Juan, Jr. et al. | |
| 6,981,958 B1 | 1/2006 | Gharib et al. | 604/8 |
| 6,989,007 B2 | 1/2006 | Shadduck | 606/4 |
| 7,041,077 B2 | 5/2006 | Shields | 604/8 |
| 7,090,681 B2 | 8/2006 | Weber | |
| 7,094,225 B2 | 8/2006 | Tu et al. | |
| 7,135,009 B2 | 11/2006 | Tu et al. | |
| 7,160,264 B2 | 1/2007 | Lisk, Jr. et al. | |
| 7,163,543 B2 | 1/2007 | Smedley et al. | |
| 7,186,232 B1 * | 3/2007 | Smedley et al. | 604/8 |
| 7,192,412 B1 | 3/2007 | Zhou et al. | |
| 7,207,965 B2 | 4/2007 | Simon | |
| 7,220,238 B2 | 5/2007 | Lynch et al. | |
| 7,273,475 B2 | 9/2007 | Tu et al. | |
| 7,297,130 B2 | 11/2007 | Bergheim et al. | |
| 7,331,984 B2 | 2/2008 | Tu et al. | |
| 7,431,710 B2 | 10/2008 | Tu et al. | |
| 7,488,303 B1 | 2/2009 | Haffner et al. | |
| 7,857,782 B2 | 12/2010 | Tu et al. | |
| 2002/0013546 A1 | 1/2002 | Grieshaber et al. | |
| 2002/0013572 A1 | 1/2002 | Berlin | |
| 2002/0072673 A1 | 6/2002 | Yamamoto et al. | 600/452 |
| 2002/0111608 A1 | 8/2002 | Baerveldt et al. | |
| 2002/0128613 A1 | 9/2002 | Nakayama | 604/294 |
| 2002/0133168 A1 | 9/2002 | Smedley et al. | 606/108 |
| 2002/0143284 A1 | 10/2002 | Tu et al. | 604/9 |
| 2002/0177856 A1 | 11/2002 | Richter et al. | 606/108 |
| 2002/0193725 A1 | 12/2002 | Odrich | 604/8 |
| 2003/0055372 A1 | 3/2003 | Lynch et al. | 604/8 |
| 2003/0060752 A1 | 3/2003 | Bergheim et al. | |
| 2003/0097151 A1 | 5/2003 | Smedley et al. | |
| 2003/0097171 A1 | 5/2003 | Elliott | |
| 2003/0135149 A1 | 7/2003 | Cullen et al. | |
| 2003/0181848 A1 | 9/2003 | Bergheim et al. | |
| 2003/0187384 A1 | 10/2003 | Bergheim et al. | |
| 2003/0187385 A1 | 10/2003 | Bergheim et al. | 604/27 |
| 2003/0208163 A1 | 11/2003 | Yaron et al. | |
| 2003/0229303 A1 | 12/2003 | Haffner et al. | 604/8 |
| 2003/0236483 A1 | 12/2003 | Ren | 604/8 |
| 2003/0236484 A1 | 12/2003 | Lynch et al. | 604/8 |
| 2004/0015140 A1* | 1/2004 | Shields | 604/289 |
| 2004/0024345 A1 | 2/2004 | Gharib et al. | 604/8 |
| 2004/0050392 A1 | 3/2004 | Tu et al. | 128/898 |
| 2004/0088048 A1 | 5/2004 | Richter et al. | 623/4.1 |
| 2004/0102729 A1 | 5/2004 | Haffner et al. | 604/8 |
| 2004/0147870 A1 | 7/2004 | Burns et al. | |
| 2004/0148022 A1 | 7/2004 | Eggleston | |
| 2004/0193095 A1 | 9/2004 | Shadduck | 604/8 |
| 2004/0193262 A1 | 9/2004 | Shadduck | 623/4.1 |
| 2004/0210181 A1 | 10/2004 | Vass et al. | 604/8 |
| 2004/0216749 A1 | 11/2004 | Tu et al. | |
| 2004/0225250 A1 | 11/2004 | Yablonski | 604/8 |
| 2004/0236343 A1 | 11/2004 | Taylor et al. | 606/108 |
| 2004/0249333 A1 | 12/2004 | Bergheim et al. | 604/8 |
| 2004/0254517 A1 | 12/2004 | Quiroz-Mercado et al. | 604/8 |
| 2004/0254519 A1 | 12/2004 | Tu et al. | 604/8 |
| 2004/0254520 A1 | 12/2004 | Porteous et al. | |
| 2004/0254521 A1 | 12/2004 | Simon | 604/8 |
| 2004/0260228 A1 | 12/2004 | Lynch et al. | |
| 2005/0008673 A1 | 1/2005 | Snyder et al. | |

| | | | |
|---|---|---|---|
| 2005/0049578 A1 | 3/2005 | Tu et al. | |
| 2005/0090806 A1 | 4/2005 | Lynch et al. | 604/523 |
| 2005/0090807 A1 | 4/2005 | Lynch et al. | |
| 2005/0119601 A9 | 6/2005 | Lynch et al. | 604/8 |
| 2005/0119636 A1 | 6/2005 | Haffner et al. | 604/500 |
| 2005/0119737 A1 | 6/2005 | Bene et al. | |
| 2005/0143817 A1 | 6/2005 | Hunter et al. | 623/11.11 |
| 2005/0149080 A1 | 7/2005 | Hunter et al. | 606/155 |
| 2005/0175663 A1 | 8/2005 | Hunter et al. | 424/423 |
| 2005/0181011 A1 | 8/2005 | Hunter et al. | 424/423 |
| 2005/0181977 A1 | 8/2005 | Hunter et al. | 514/2 |
| 2005/0182350 A1 | 8/2005 | Nigam | 604/8 |
| 2005/0191331 A1 | 9/2005 | Hunter et al. | 424/423 |
| 2005/0192527 A1 | 9/2005 | Gharib et al. | 604/8 |
| 2005/0250788 A1 | 11/2005 | Tu et al. | |
| 2005/0266047 A1 | 12/2005 | Tu et al. | |
| 2005/0273033 A1 | 12/2005 | Grahn et al. | 604/9 |
| 2005/0277864 A1 | 12/2005 | Haffner et al. | 604/8 |
| 2005/0288619 A1 | 12/2005 | Gharib et al. | 604/8 |
| 2006/0032507 A1 | 2/2006 | Tu et al. | |
| 2006/0069340 A1 | 3/2006 | Simon | |
| 2006/0074375 A1 | 4/2006 | Bergheim et al. | |
| 2006/0084907 A1 | 4/2006 | Bergheim et al. | |
| 2006/0116626 A1 | 6/2006 | Smedley et al. | |
| 2006/0155238 A1 | 7/2006 | Shields | |
| 2006/0173397 A1 | 8/2006 | Tu et al. | |
| 2006/0195055 A1 | 8/2006 | Bergheim et al. | |
| 2006/0195056 A1 | 8/2006 | Bergheim et al. | |
| 2006/0200113 A1 | 9/2006 | Haffner et al. | |
| 2006/0235367 A1 | 10/2006 | Takashima et al. | 604/541 |
| 2006/0241580 A1 | 10/2006 | Mittelstein et al. | |
| 2006/0241749 A1 | 10/2006 | Tu et al. | |
| 2007/0088424 A1 | 4/2007 | Greenberg | |
| 2007/0149915 A1 | 6/2007 | Yablonski | |
| 2010/0274259 A1* | 10/2010 | Yaron et al. | 606/108 |

FOREIGN PATENT DOCUMENTS

| | | |
|---|---|---|
| EP | 1173124 | 1/2002 |
| EP | 1173125 | 1/2002 |
| EP | 1173126 | 1/2002 |
| EP | 1278492 | 1/2002 |
| EP | 1184010 | 3/2002 |
| EP | 1292256 | 1/2003 |
| EP | 1310222 | 3/2003 |
| EP | 1310222 | 5/2003 |
| EP | 1418868 | 5/2004 |
| EP | 1477146 | 5/2004 |
| EP | 1473004 | 11/2004 |
| EP | 1477146 | 11/2004 |
| EP | 1545655 | 11/2004 |
| EP | 1977724 | 1/2007 |
| EP | 2027837 | 1/2009 |
| GB | 2101891 | 1/1983 |
| RU | 2018289 C1 | 8/1994 |
| RU | 2056818 C1 | 3/1996 |
| RU | 2074686 C1 | 3/1997 |
| RU | 2074687 C1 | 3/1997 |
| RU | 2157678 C1 | 10/2000 |
| WO | 89/00869 | 2/1989 |
| WO | 91/12046 | 8/1991 |
| WO | 92/19294 | 11/1992 |
| WO | 94/09721 | 5/1994 |
| WO | 94/09837 | 5/1994 |
| WO | 94/13234 | 6/1994 |
| WO | WO 95/08310 | 3/1995 |
| WO | 96/20742 | 7/1996 |
| WO | 96/36377 | 11/1996 |
| WO | 98/23237 | 6/1998 |
| WO | 98/30181 | 7/1998 |
| WO | 99/26567 | 6/1999 |
| WO | 00/06223 | 2/2000 |
| WO | WO0064389 | 4/2000 |
| WO | 00/64511 | 11/2000 |
| WO | WO0178656 | 10/2001 |
| WO | 02/36052 | 5/2002 |
| WO | 02/070045 | 9/2002 |
| WO | 02/074052 | 9/2002 |
| WO | WO02074052 | 9/2002 |
| WO | 02/080811 | 10/2002 |
| WO | 02/080829 | 10/2002 |
| WO | WO 02/080811 A2 * | 10/2002 |
| WO | 02/087418 | 11/2002 |
| WO | 02/087479 | 11/2002 |
| WO | 02/089699 | 11/2002 |
| WO | 02/102274 | 12/2002 |
| WO | 03/015659 | 2/2003 |
| WO | 03/015667 | 2/2003 |
| WO | WO03015659 | 2/2003 |
| WO | WO 03/041622 | 5/2003 |
| WO | 03/073968 | 9/2003 |
| WO | 03/099175 | 12/2003 |
| WO | 2004/026347 | 4/2004 |
| WO | WO2004/043231 | 5/2004 |
| WO | 2004/056294 | 7/2004 |
| WO | 2004/060219 | 7/2004 |
| WO | 2004/062469 | 7/2004 |
| WO | 2004/110391 | 12/2004 |
| WO | 2005/016418 | 2/2005 |
| WO | WO2005016148 | 2/2005 |
| WO | 2005/046516 | 5/2005 |
| WO | WO 2005/046782 | 5/2005 |
| WO | WO2005/055873 | 6/2005 |
| WO | WO2005/107664 | 11/2005 |
| WO | WO2005/107845 | 11/2005 |
| WO | WO 2005105197 | 11/2005 |
| WO | WO2006/012421 | 2/2006 |
| WO | WO2006/036715 | 4/2006 |
| WO | 2007/087061 | 8/2007 |
| WO | 2007/115259 | 10/2007 |
| WO | WO2007130393 | 11/2007 |
| WO | 2008/061043 | 5/2008 |

OTHER PUBLICATIONS

Cohen, V.M., et al., "First day post-operative review following uncomplicated phacoemulsification," Eye, 12(4):634-636, (1998).

Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession Nbr. 12409716 [351].

Dinakaran, S., et al., "Is the first post-operative day review necessary following uncomplicated phacoemulsification surgery?" Eye, 14(3A):364-366, (2000).

Einmahl, S., et al., "Evaluation of a novel biomaterial in the suprachoroidal space of the rabbit eye," Investigative Opthamology and Visual Sciences, 43:1533-1539, (2002).

Gross, R.L., et al., "Surgical therapy of chronic glaucoma in aphakia and pseudophakia," Ophthalmology, 95:1195-1201, (1988).

Hildebrand, G.D., et al., "Efficacy of anterior chamber decompression in controlling early intraocular pressure spikes after uneventful phacoemulsification," Journal of Cataract and Refractive Surgery, 29:1087-1092, (2003).

Howorth, D.J., "Feasibility study for a micromachined glaucoma drainage device," Cranfield University School of industrial and manufacturing science MSc Thesis Academic Year 2001-2002 Sep. 13, 2002.

Hylton, C. and A. Robin et al., "Update on prostaglandin analogs," Current Opinion in Opthamology, 14:65-69, (2003).

Jordan, J. "A novel approach to suprachoroidal drainage for the surgical treatment of intractable glaucoma," Journal of Glaucoma, 15:200-205, (2006).

Lee et al. "Magnetic resonance imaging of the aqueous flow in eyes implanted with the trabeculo-suprachoroidal glaucoma seton," Investigative Opthamology and Visual Sciences 33:948 (1992).

Mehta, K.R., "The suprachoroidal hema wedge in glaucoma surgery," American Academy of Ophthalmology meeting 1977 pp. 144.

Rosenberg, L. and T. Krupin, *The Glaucomas*, Second Edition, Chapter 88, Eds., Ritch, R., et al., Mosby, St. Louis, MO., pp. 1783-1807, (1986).

"The Solx Gold Micro-shunt (GMS) Treatment," Solx clinical literature hand-out from Industry Show, Feb. 2006.

Srinivasan, R. et al., "Microbial contamination of the anterior chamber during phacoemulsification," Journal of Cataract and Refractive Surgery, 28:2173-2176, (2002).

Toris, C., et al., "Aqueous humor dynamics in the aging human eye," American Journal of Opthamology, 127:407-412, (1999).

Yablonski, M.E., "Some thoughts on the pressure dependence of uveoscleral flow," Journal of Glaucoma, 12(1):90-92, (2003).

Yablonski, M.E., "Trabeculectomy with Internal Tube Shunt: a novel glaucoma surgery," Journal of Glaucoma, 14:91-97, (2005).

Fuchs E. "Detachment of the choroid inadvertently during cataract surgery," von Graefes Arch Ophthalmol, 51:199-224 (1900) [German with English Languauge abstract].

Heine I. "Cyclodialysis, a new glaucoma operation," Dtsch Med Wochenschr, 31:824-826 (1905) [German with English Languauge abstract].

Karlen et al., "Deep sclerectomy with collagen implant:medium term results" Br. J. Ophthalmol, 83(1):6-11 (1999).

Kozlov et al. "Nonpenetrating deep sclerectomy with collagen," Eye Microsurgery 3:44-46 (1990). [Russian with English translation].

Bick, M. "Use of Tantalum for Ocular Drainage," Arch Ophthal. Oct. 1949; 42(4): 373-88.

Bietti "The present state of the use of plastics in eye surgery" Acta Ophthalmol (Copenh) 1955; 33(4):337-70.

Gills "Cyclodialysis implants" South Med J. 1967 60(7):692-5.

Gills et al. "Action of cyclodialysis utilizing an implant studied by manometry in a human eye" Exp Eye Res 1967; 6:75-78.

Jordan et al. "A Novel Approach to Suprachoroidal Drainage for the Surgical Treatment of Intractable Glaucoma," J. Glaucoma 2006; 15:200-205.

Klemm et al. "Experimental use of space-retaining substances with extended duration: functional and morphological results" Graefes Arch Clin Exp Ophthalmol Sep. 1995; 233(9):592-7.

Krejci "Cyclodialysis with hydroxymethyl methacrylate capillary strip (HCS). Animal experiments with a new approach in glaucoma drainage surgery" Ophthalmologica 1972; 164(2):113-21.

Losche "Proposals for improvement of cyclodialysis" Klin Monatsblatter Augenheilkd Augenarztl Fortbild 1952, 121(6):715-6 [Article in German; English translation provided].

Nesterov AP et al. "Surgical stimulation of the uveoscleral outflow. Experimental studies on enucleated human eyes" Acta Opthalmol (Copenh) June; 57(3):409-17 (1979).

Ozdamar et al. "Suprachoroidal seton implantation in refractory glaucoma: a novel surgical technique" J. Glaucoma Aug. 2003; 12(4):354-9.

Pinnas et al. "Cyclodialysis with teflon tube implants" Am J. Ophthalmol 1969 Nove; 68(5):879-883.

Row, H., "Operation to Control Galucoma," (1934) Arch. Ophthal 12, 325.

Troncosco UM Cyclodialysis with insertion of metal implant in treatment of glaucoma Preliminary report Arch. Ophth. 23:270, 1940.

Emi et al. "Hydrostatic pressure of the suprachoroidal space" Invest. Ophthal. Visual Sci. 30(2):233-238 (1989).

Barsky et al. "Evaluation of absorbable gelatin film (Gelfilm) in cyclodialysis clefts" Arch. Ophth. 60(6): 1044-1052,1958.

Brown et al., "Internal Sclerectomy for Glaucoma Filtering Surgery with an Automated Trephine," Archives of Ophthalmology, vol. 105, Jan. 1987,133-136.

Chiou et al. "Ultrasound biomicroscopy of eyes undergoing deep sclerectomy with collagen implant" Br J Ophthalmol 80 (1996), pp. 541-544.

Demailly et al. "Non-penetrating deep sclerectomy (NPDS) with or without collagen device (CD) in primary open-angle glaucoma: middle-term retrospective study" International Ophthalmology 20: 131-140, 1997.

Draeger "Chirurgische Maβnahmen bei kongenitalem Glaukom" (Surgical Interventions in Congenital Glaucoma) Klin Monatsbl Augenheilkd 1993; 202(5): 425-427 [Article in German with English summary included].

Ellis, RA "A Reduction Of Intraocular Pressure Using Plastics In Surgery" Am J Ophth. 50; 1960, 733-746.

Gills, "Cyclodialysis Implants In Human Eyes" Am J Ophth 61:1966,841-846.

Goldberg "Management Of Uncontrolled Glaucoma With The Molteno System" Australian and New Zealand Journal of Ophthalmology 1987; 15: 97-107.

Harrington "Cataract and glaucoma. Management of the coexistent conditions and a description of a new operation combining lens extraction with reverse cyclodialysis." Am J Ophthalmol. May 1966;61(5 Pt 2):1134-40.

Klemm et al. "Die Ultraschallbiomikroskopie als Kriterium der Funktionsprüfung des suprachorioidalen Spaltes nach kammerwinkelchirurgischen Eingriffen (Ultrasound Biomicroscopic Imaging for Assessment of the Suprachoroidal Cleft after Angle Surgery)" Klinische Monatsblätter für Augenheilkunde 1997; 210: 74-77 [Article in German with English summary included].

Krejci L. "Microdrainage of anterior chamber of eye glaucoma operation using hydron capillary drain." Acta Univ Carol Med Monogr. 1974;(61):1-90.

Kupfer "Studies on intraocular pressure. I. A technique for polyethylene tube implantation into the anterior chamber of the rabbit." Arch Ophthalmol. Apr. 1961;65:565-70.

La Rocca "Gonioplasty in Glaucoma*A Preliminary Report" Br J Ophth 46:1962, 404-415.

Law et al., "Retinal Complications After Aqueous Shunt Surgical Procedures for Glaucoma" Arch Ophthal.; Dec. 1996; vol. 114:1473-1480.

Marx et al., "Use of the Ganciclovir Implant in the Treatment of Recurrent Cytomegalovirus Retinitis" Arch Ophthal.; Jul. 1996; vol. 114:815-820.

McPherson "Combined Trabeculotomy and Cataract Extraction as a Single Operation" Tr. Am. Ophth. Soc., vol. LXXIV, 1976.

Miki, MD et al., "Intraocular Cannula for Continuous, Chronic Drug Delivery-Histopathic Observations and Function" Arch Ophthal.; May 1985; vol. 103:712-717.

Molteno et al. "Long tube implants in the management of glaucoma" South African Medical Journal, Jun. 26, 1976;50(27):1062-6.

Molteno et al. "The Vicryl tie technique for inserting a draining implant in the treatment of secondary glaucoma. " Australian and New Zealand Journal of Ophthalmology 1986; 14: 343-354.

Moses RA "Detachment of ciliary body-anatomical and physical considerations" Investigative Ophthalmology & Visual Science, Assoc. For Research In Vision and Ophthalmology, US, vol. 4, No. 5, Oct. 1, 1965, 935-941.

Nguyen et al., "Complications of Baerveldt Glaucoma Drainage Implants" Arch Ophthal.; May 1998; vol. 116:571-575.

O'Brien et al. "Cyclodialysis" Arch Ophthal. 1949;42(5):606-619.

Portney GL, "Silicone elastomer implantation cyclodialysis." Arch Ophthalmol 1973; 89: 10-12.

Pruett et al., "The Fishmouth Phenomenon-II. Wedge Scleral Buckling" Arch Ophthal.; Oct. 1977; vol. 95:1782-1787.

Qadeer "Acrylic Gonio-Subconjunctival Plates in Glaucoma Surgery" Br J Ophthalmol. Jun. 1954; 38(6): 353-356.

Richards et al. "Artificial Drainage Tubes For Glaucoma" Am J Ophth 60:1965,405-408.

Sampimon "A New Approach to Filtering Glaucoma Surgery" Ophthalmologica (Basel) 151: 1966, 637-644.

Sourdille et al. "Reticulated hyaluronic acid implant in non-perforating trabecular surgery." J Cataract Refract Surg 25: 332-339. (1999).

Toris et al. "Effect of intraocular pressure on uveoscleral outflow following cyclodialysis in the monkey eye." Investigative Ophthalmology & Visual Science. 26 (1985) 1745-1749.

Veen et al. "The gonioseton, a surgical treatment for chronic glaucoma" Documenta Ophthalmologica vol. 75, Nos. 3-4, 365-375.

Zhou et al. "A trabecular bypass flow hypothesis" J Glaucoma. 14(1):74-83 (2005).

Burchfield JC, Kass MA, Wax MB. Primary valve malfunction of the Krupin eye valve with disk. J Glaucoma. Jun. 1997;6(3):152-6.

Chylack LT, Bellows AR. Molecular sieving in suprachoroidal fluid formation in man. Invest Ophthalmol Vis Sci 17: 420, 1978.

Collaborative Normal-Tension Study Group. Comparison of glaucomatous progression between untreated patients with normal-tension glaucoma and patients with therapeutically reduced intraocular pressures. Am J Ophthalmol 1998;126:487-97.

Fanous MM, Cohn RA. Propionibacterium endophthalmitis following Molteno tube repositioning. J Glaucoma. Aug. 1997;6(4):201-2.

Gordon MO, Kass. MA, for the Ocular Hypertension Treatment Study Group. The Ocular Hypertension Treatment Study. Design and baseline description of the participants. Arch Ophthalmol 1999:573-83.

Grant, W.M., MD, Further Studies on Facility of Flow Through the Trabecular Meshwork, A.M.A. Archives of Ophthalmololgy, Oct. 1958, vol. 60, pp. 523-533.

Harper SL, Foster CS. Intraocular lens explantation in uveitis. Int Ophthalmol Clin. 2000 Winter; 40(1):107-16.

Heijl A, Leske MC, Bengtsson B, et al for the Early Manifest Glaucoma Trial Group. Reduction of intraocular pressure and glaucoma progression. Results from the Early Manifest Glaucoma Trial. Arch Ophthalmol 2002;120:1268-79.

Hoskins, et al., "Aqueous Humor Outflow", Becker-Shaffer's Diagnosis and Therapy of the Glaucomas, 6th Edition, Chapter 4, pp. 41-66, 1989.

Javitt JC, Chiang YP. Preparing for managed competition. Utilization of ambulatory eye care visits to ophthalmologists. Arch Ophthalmol 1993;111:1034-5.

Jay JL, Allan D. The benefit of early trabeculectomy versus conventional management in primary open-angle glaucoma relative to severity of disease. Eye 1989; 3:528-35.

Kass Ma, Heuer DK, Higginbotham EJ, et al for the Ocular Hypertension Treatment Study Group. The Ocular HypertensionTreatment Study. A randomized trial determines that topical ocular hypotensive medication delays or prevents the onset of primary open-angle glaucoma. Arch Ophthalmol 2002;120:701-13.

Lee Ky. Trabeculo-suprachoroidal shunt for treating recalcitrant and secondary glaucoma. Presented at the American Academy of Ophthalmology Annual Meeting, Anaheim, CA, 1991.

Leske MC, Heijl A, Hussein M, et al for the Early Manifest Glaucoma Trial Group. Factors for glaucoma progression and the effect of treatment. The Early Manifest Glaucoma Trial. Arch Ophthalmol 2003;121:48-56.

Lichter PR, Musch DC, Gillespie BW, et al and the CIGTS Study Group. Interim clinical outcomes in the Collaborative Initial Glaucoma Treatment Study comparing initial treatment randomized to medications or surgery. Ophthalmology 2001;108:1943-53.

Migdal C, Gregory W, Hitchings R. Long term functional outcome after early surgery compared with laser and medicine in open-angle glaucoma. Ophthalmology 1994;101:1651-7.

Miglior S, Zeyen T, Pfeiffer N, et al for the European Glaucoma Prevention Study Group. The European Glaucoma Prevention Study design and baseline description of the participants. Ophthalmology 2002;109:1612-21.

Olson, Timothy W., et al., Cannulation of the Suprachoroidal Space: A Novel Drug Delivery Methodology to the Posterior Segment, American Journal of Ophthalmology, vol. 142, No. 5, Nov. 2006, pp. 777-787.e2.

Quigley Ha, Vitale S. Models of open-angle glaucoma prevalence and incidence in the United States. Invest Ophthalmol Vis Sci 1997; 38:83-91.

Ritch, et al., "Uveoscleral Outflow", The Glaucomas. St. Louis: Mosby, 1996; pp. 337-343.

Rohen, Johannes W., Anatomy of the Aqueous Outflow Channels, Glaucoma, vol. 1, Chapter 14, pp. 277-296, Edited by J.E. Cairns, Grune & Stratton, Harcourt Brace Jovanovich Publishers, 1986.

Rowan, Patrick J., MD, Combined Cyclodialysis and Cataract Surgery, Ophthalmic Surgery and Lasers, Dec. 1998, vol. 29, No. 12, pp. 962-968 (9 pages).

Schappert S. Office visits for glaucoma: United States, 1991-92. Advance data from vital and health statistics. vol. 262. Hyattsville, MD: National Center for Health Statistics, 1995.

Shaffer RN, Weiss DI. Concerning cyclodialysis and hypotony. Arch Ophthalmol 68: 25, 1962.

Sommer A, Tielsch JM, Katz J, et al. Racial differences in the cause-specific prevalence of blindness in east Baltimore. N Engl J Med 1991;325:1412-7.

Suguro K, Tons CB, Pederson JE. Uveoscleral outflow following cyclodialysis in the monkey eye using a fluorescent tracer. Invest Ophthalmol Vis Sci 1985: 26, 810.

The Advanced Glaucoma Intervention Study (AGIS): 7. The relationship between control of intraocular pressure and visual field deterioration. The AGIS Investigators. Am J Ophthalmol 2000;130:429-40.

The Glaucoma Laser Trial (GLT) and Glaucoma Laser Trial Follow-up Study: 7. Results. Am J Ophthahnol 1995;120:718-31.

The Glaucoma Laser Trial (GLT). 2. Results of argon laser trabeculoplasty versus topical medicines. The Glaucoma Laser Trial Research Group. Ophthalmology 1990;97:1403-13.

Tielsch JM, Sommer A, Katz J, et al. Racial variations in the prevalence of primary open-angle glaucoma. The Baltimore Eye Survey. JAMA 1991;266:369-74.

Toris CB. Extravascular albumin concentration of the uvea. Invest Ophthalmol Vis Sci 1990; 31:43.

Troncoso, Manuel U., Tantalum implants for inducing hypotony, Am Journal of Ophthalmology, vol. 32(4):499-508 (1949).

Wagner, Justin A., et al., Characterization of Uveoscleral Outflow in Enucleated Porcine Eyes Perfused under Constant Pressure, Invest Ophthalmol Vis Sci., Published in edited form in Sep. 2004, vol. 45, Issue 9, pp. 3203-3206.

* cited by examiner

OCULAR PRESSURE REGULATION

RELATED APPLICATIONS

This application is a continuation of U.S. application Ser. No. 10/712,277, filed Nov. 14, 2003 now U.S. Pat No. 7,291,125, entitled "OCULAR PRESSURE REGULATION"By Minas Coreneo.

This application also is related to U.S. application Ser. No. 10/579,330, filed Nov. 12, 2004, entitled "OCULAR PRESSURE REGULATION" by Minas Coroneo; and to U.S. application Ser. No. 11/615,615, filed the same day herewith, entitled "OCULAR PRESSURE REGULATION" by Minas Coroneo.

Where permitted, the subject matter of each of the above noted applications is incorporated by reference in its entirety by reference thereto.

FIELD OF THE INVENTION

This invention is directed to therapeutic methods and devices for the treatment of glaucoma. In particular, this invention is concerned with the use of a shunt or drain for the treatment of glaucoma. In another aspect this invention is concerned with ocular pressure spike shunts and use of the same in ocular surgery.

BACKGROUND OF THE INVENTION

The glaucomas are a common group of blinding conditions usually associated with elevated intraocular pressure. This elevated pressure in the eye may be regarded as a disorder of the drainage system of the eye which gives rise to the glaucomas.

Aqueous humor of the eye ("aqueous") is a flowing liquid fluid (composed of sodium, chloride, bicarb, amino acids, glucose, ascorbic acid, and water) that is actively secreted by the ciliary body and flows out past the iris into the anterior chamber (are between the lens/iris and the cornea). The aqueous drains out through angle formed by the iris and the sclera into a meshwork call the trabeculum, and from there into the canal of Schlemm and then into the episcleral veins. Uveosclera drainage also occurs. Normal intraocular pressure (IOP) of aqueous in anterior chamber is between 10 and 20 mm Hg. Prolonged IOPs of greater than 21 mm Hg are associated with damage to optic nerve fibers.

In some cases of glaucoma the cause can be found: the trabecular meshwork becomes blocked by pigment or membrane. In other cases, blockage is due to a closure of the angle between the iris and the cornea. This angle type of glaucoma is referred to as "angle-closure glaucoma". In the majority of glaucoma cases, however, called "open angle glaucoma", the cause is unknown.

Elevated intraocular pressure results in the death of retinal ganglion cells (which convey retinal information to the brain) resulting in a characteristic pattern of loss of the field of vision, progressing to tunnel vision and blindness if left untreated.

Treatment of glaucoma consists predominantly of methods to lower the intraocular pressure (pharmacological, trabecular meshwork laser and surgery to drain fluid from the eye). More recently protection of the retinal ganglion cells by neuroprotective agents has been attempted.

Although pharmacological treatments of glaucoma have improved, they have important implications for the patient's quality of life, have compliance issues which are important in the elderly (in whom glaucoma is prevalent), expose the patient of glaucoma to side effects, and over a lifetime are costly.

Surgery for glaucoma treatment is usually a trabeculectomy in which a fistula is created to drain fluid from the anterior chamber to the subconjunctival space near the limbus, creating a bulge in the conjunctiva known as a bleb. Frequently scarring occurs and attempts to counter this with antimetabolites such as Mitomycin C have met with some success. In recalcitrant cases, glaucoma implants, drainage, shunt or valve devices have been developed e.g. Molteno (U.S. Pat. No. 4,457,757), Krupin (U.S. Pat. No. 5,454.746) and Baerveldt (U.S. Pat. No. 5,178,604). These suffer from similar problems of scarring (Classen L, Kivela T, Tarkkanen "A Histopathologic and immunohistochemical analysis of the filtration bleb after unsuccessful glaucoma seton implantation" *Am J Ophthalmol,* 1996;122:205-12) around the external opening of the tube devices in the subconjunctival space—the development of a large number of these devices is testament to the fact that many fail in the longer term. In these devices a drainage tube is located in the anterior chamber and is in fluid communication with the sclera or a surgically created subconjunctival space.

Whereas cataract surgery has been revolutionized in the last two decades, improvements in glaucoma surgery have been slower. Antifibrotic agents have improved the success rate of conventional filtration surgery (trabeculectomy), but with increased bleb leaks, blebitis, endophthalmitis and hypotensive maculopathy. Glaucoma shunts have had limited success in eyes that have "failed" multiple standard procedures. However complications with malpositioned tubes, erosion and strabismus persist. A considerable issue is the lack of reproducibility and predictability in achieving the desired target intraocular pressure (IOP). Final IOP is largely determined by healing which can be unpredictable—in view of vast biological variations, it is impossible to predict which eyes will rapidly scar causing failure and which will fail to heal resulting in prolonged post-operative hypotony. Scarring remains a significant problem in all these external drainage proposals, where aqueous drains into the conjunctiva, or surgical chambers in the sciera.

The introduction of a new class of antiglaucoma drugs, the prostaglandin analogues, has resulted in acknowledgment of the importance of the uveoscleral pathway in drainage of fluid form the eye (Hylton C, Robin A L "Update on prostaglandin analogs" *Curr Opin Ophthalmol,* 2003;14:65-9). Uveoscleral flow where aqueous humor flows through the interstitium of the ciliary muscle into the suprachoroidal space (a potential space between the choroids and sclera) and out through the sclera into the connective tissue of the orbit may account for 54% of outflow young healthy humans (Toris C B, Yablonski M E, Wang Y L, Camras C B "Aqueous humor dynamics in the aging human eye" *Am J Ophthalmol,* 1999;127:407-12).

Cyclodialysis, the separation of the ciliary body from the scleral spur and underlying sclera, creates free communication between the anterior chamber and the suprachoroidal space and enhances uveoscleral flow. It has long been known that cyclodialysis can cause a profound reduction of intraocular pressure—initially (Fuchs E. "Detachment of the choroid inadvertently during cataract surgery" [German] *von Graefes Arch Ophthalmol,* 1900;51:199-224) cyclodialysis was recognized as a complication of cataract surgery. Deliberate creation of a cyclodialysis cleft for treating elevated intraocular pressure in uncontrolled glaucoma was first described as a surgical procedure in 1905 (Heine I. "Cyclodialysis, a new glaucoma operation" [German]) *Dtsch Med Wochenschr,* 1905;31:824-826). Since such clefts can heal and close spontaneously a number of devices have been used to keep them open, including platinum wire, horse hair, magnesium strips, tantalum foil, Supramid®, gelatin film, Teflon®, silicone and polymethylmethacrylate (Rosenberg L F, Krupin T. "Implants in glaucoma surgery" Chaptter 88, *The Glaucomas*, Ritch R, Shields B M, Krupin T Eds. 2$^{nd}$ Edition Mosby St Louis 1986) and Hema (Mehta K R. "The suprachoroidal Hema wedge in glaucoma surgery" American Academy of Ophthalmology meeting 1977, pp 144). However the success rate of such approaches has been low (as low as 15%, Rosenburg & Krupin ibid and Gross R L, Feldman R M, Spaeth G L, et al "Surgical therapy of chronic glaucoma in aphakia and pseudophakia" *Ophthalmology,* 1988;95:1195-201). Failure was due to uncontrolled low pressure (hypotony) with consequential macular edema, bleeding (hyphema) and inadequate pressure control.

The device and method of a first aspect of this invention takes advantage of the methods used in cataract surgery to develop a minimally invasive glaucoma procedure—thus small, self sealing incisions and materials that are biocompatible and foldable so that they fit through small openings will reduce surgical trauma and time. The controlled draining of aqueous into the suprachoroidal space according to this invention provides some predictability of outcome and overcomes scarring problems that have plagued glaucoma implants in the past.

The most frequent complication following modern cataract surgery with phacoemulsification, requiring specific treatment is elevated intraocular pressure (Cohen V M, Demetria H, Jordan K, Lamb R J, Vivian A J. :First day post-operative review following uncomplicated phacoemulsification" *Eye,* 1998;12 ( Pt 4):634-6, and Dinakaran S, Desai S P, Raj P S. "Is the first post-operative day review necessary following uncomplicated phacoemulsification surgery?" *Eye,* 2000 Jun.; 14 ( Pt 3A):364-6). The increase may be marked and typically peaks at 5 to 7 hours before returning to near normal levels in 1 to 3 days (Hildebrand G D, Wickremasinghe S S, Tranos P G, Harris M L, Little B C. "Efficacy of anterior chamber decompression in controlling early intraocular pressure spikes after uneventful phacoemulsification" *J Cataract Refract Surg.,* 2003; 29:1087-92). Such pressure spikes can cause pain and may increase the risk of sight-threatening complications such as retinal vascular occlusion, increases loss of visual field in advanced glaucoma and ischemic optic neuropathy—effects in otherwise healthy eyes are unknown (Hildebrand G D et al, ibid).

A number of prophylactic treatments are used with limited success—these include intracameral carbachol or acetylcholine, topical timolol, dorzolamide, aproclonidine, latanoprost and systemic acetazolamide (see Hildebrand G D et al, ibid). This also exposes the patient to the risk of drug side effects, increased cost and it has been postulated that reducing the flow of aqueous humor post surgery prolongs the residence time of bacteria that frequently (46.3% of cases) contaminate the anterior chamber during surgery (Srinivasan R, Tiroumal S, Kanungo R, Natarajan M K. "Microbial contamination of the anterior chamber during phacoemulsification" *J Cataract Refract Surg,* 2002; 28:2173-6.). This may increase the risk of endophthalmitis one of the most devastating sequelae of intraocular surgery, since the bacteria are not being "flushed out" of the eye by the normal production of aqueous humour, the secretion of which has been suppressed by the drugs. Another technique is to decompress the anterior chamber by applying pressure to the posterior lip of the paracentesis wound at the appropriate time. This requires surveillance and could increase the risk of infection. Another aspect of this invention hereinafter described overcomes these problems.

SUMMARY OF THE INVENTION

According to the present invention there is provided a flexible ocular device for implantation into the eye formed of a biocompatible elastomeric material, foldable to a diameter of 1.5 mm or less, comprising a fluid drainage tube having at one end a foldable plate adapted to locate the device on the inner surface of the sclera in a suprachoroidal space formed by cyclodialysis, said drainage tube opening onto the disc at one end and opening to the anterior chamber when implanted into the eye at its other end, so as to provide aqueous pressure regulation.

Preferably the fluid drainage tube has a diameter selected to provide predetermined resistance to aqueous humor flow, for example a pressure of 10 mm Hg or less. Alternatively said tube contains a valve so as to regulate pressure of the aqueous chamber at a predetermined level, for example, at no less than 10 mm Hg.

In accordance with another embodiment of this invention there is provided a method for treating glaucoma which comprises:

providing a flexible ocular device formed of a biocompatible elastomeric material foldable to a diameter of 1.5 mm or less, comprising a fluid drainage tube having at one end a foldable plate adapted to locate the device on the inner surface of the sclera and at its other end being open so as to allow fluid communication through said tube;

forming a small self-sealing incision at the juncture of the cornea and sclera of the eye opening into the anterior chamber;

filling the anterior chamber with a viscoelastic substance;

introducing the foldable ocular device into a suprachoroidal space formed by cyclodialysis via a hollow cannula, wherein said plate locates the device on the inner surface of the sclera in the suprachoroidal space, and said drainage tube is located in the anterior chamber of the eye so as to provide aqueous humor pressure regulation; and thereafter removing said cannula and viscoelastic material from the eye.

In another aspect there is provided an ocular pressure spike shunt for insertion into an ocular paracentesis incision port following ocular surgery, comprising a flexible fluid transfer tube formed of biocompatible material, preferably biocompatible elastomeric material, so as to allow paracentesis incision closure around said tube, having an inner end and an outer end, a tubular lumen disposed between said inner end and said outer end to allow fluid communication through said tube, said lumen containing a valve for controlling pressure in the eye following ocular surgery, which valve opens permitting fluid flow through said tube when a predetermined pressure is exceeded, said shunt being configured such that on insertion into a paracentesis port said outer end is substantially flush with the surface of the cornea, and said inner end opens into the anterior chamber of the eye.

In another aspect there is provided a method for preventing ocular pressure spikes following ocular surgery wherein a paracentesis incision port is formed in the eye during said surgery, comprising introducing an ocular pressure spike shunt into said paracentesis port at the conclusion of ocular surgery, said shunt comprising a flexible fluid transfer tube formed of biocompatible material, preferably biocompatible elastomeric material, so as to allow paracentesis incision closure around said tube, having an inner end and an outer end, a tubular lumen disposed between said inner end and said outer end to allow fluid communication through said tube, said lumen containing a valve for controlling pressure in the eye following ocular surgery, which valve opens permitting fluid flow through said tube when a predetermined pressure is exceeded, said shunt being configured such that on insertion into a paracentesis port said outer end is substantially flush with the surface of the cornea, and said inner end protrudes into the anterior chamber of the eye.

DETAILED DESCRIPTION OF THE PREFERRED EMBODIMENTS OF THE INVENTION

The ocular device according to the present invention is implanted in a patient's eye using minimally invasive surgery techniques, adopted from modern cataract surgery.

Figure 1:
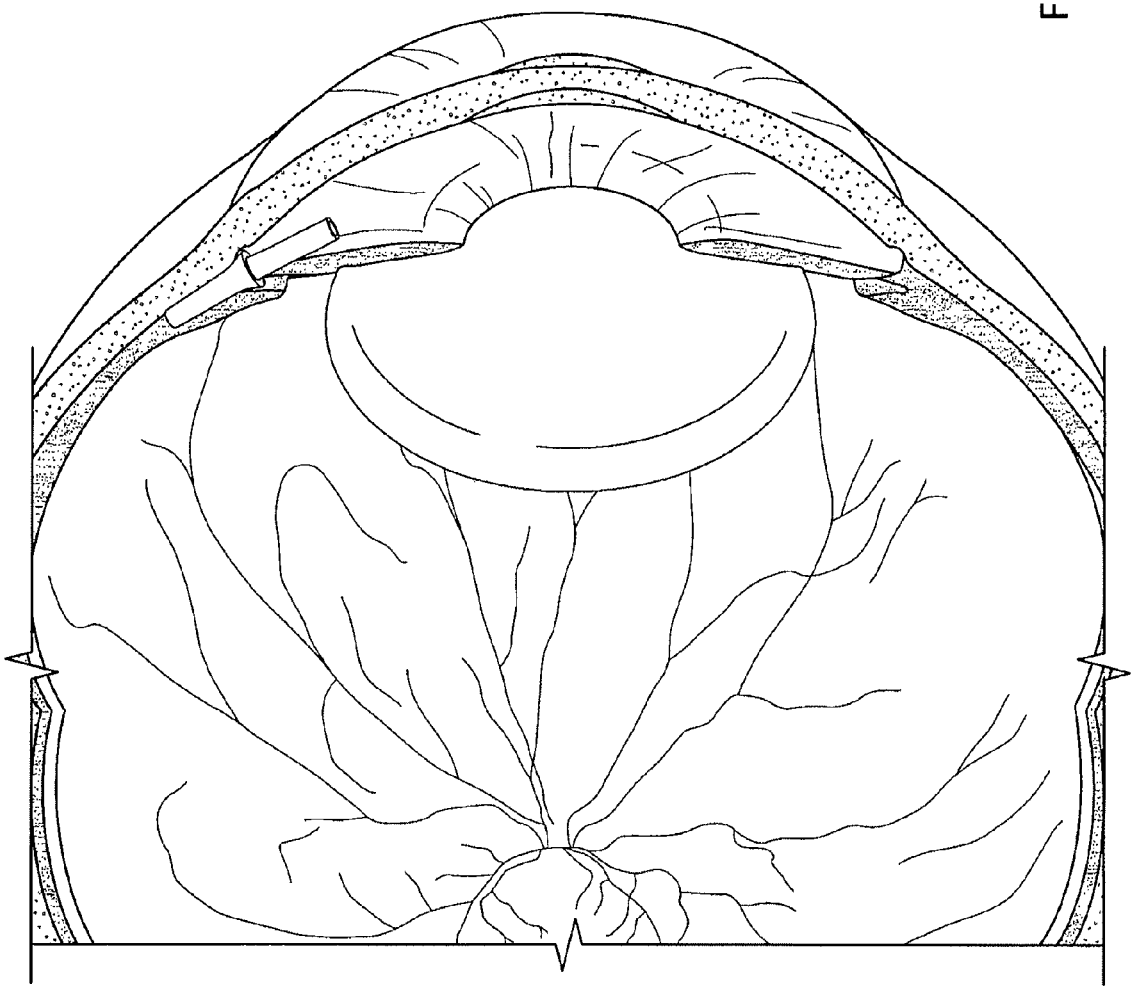
FIG. 1 shows a diagrammatic representation of a side sectional view of suprachoroidal shunt insertion using an injector.

The ocular device is formed from a biocompatible elastomeric material. Preferably, the device is made of soft surgical grade polymeric material, such as silicon or acrylic material such that the device is foldable and may be rolled up for insertion via a cannula. FIG. 1 shows a proximal end of a cannula forming a cyclodialysis. The folded device may be introduced via such a cannula The elastomeric material is selected to be sufficiently soft that it does not erode delicate underlying choroid material when inserted into the eye. Such material and ocular lenses formed therefrom are well known and used in cataract surgery.

Figure 2:
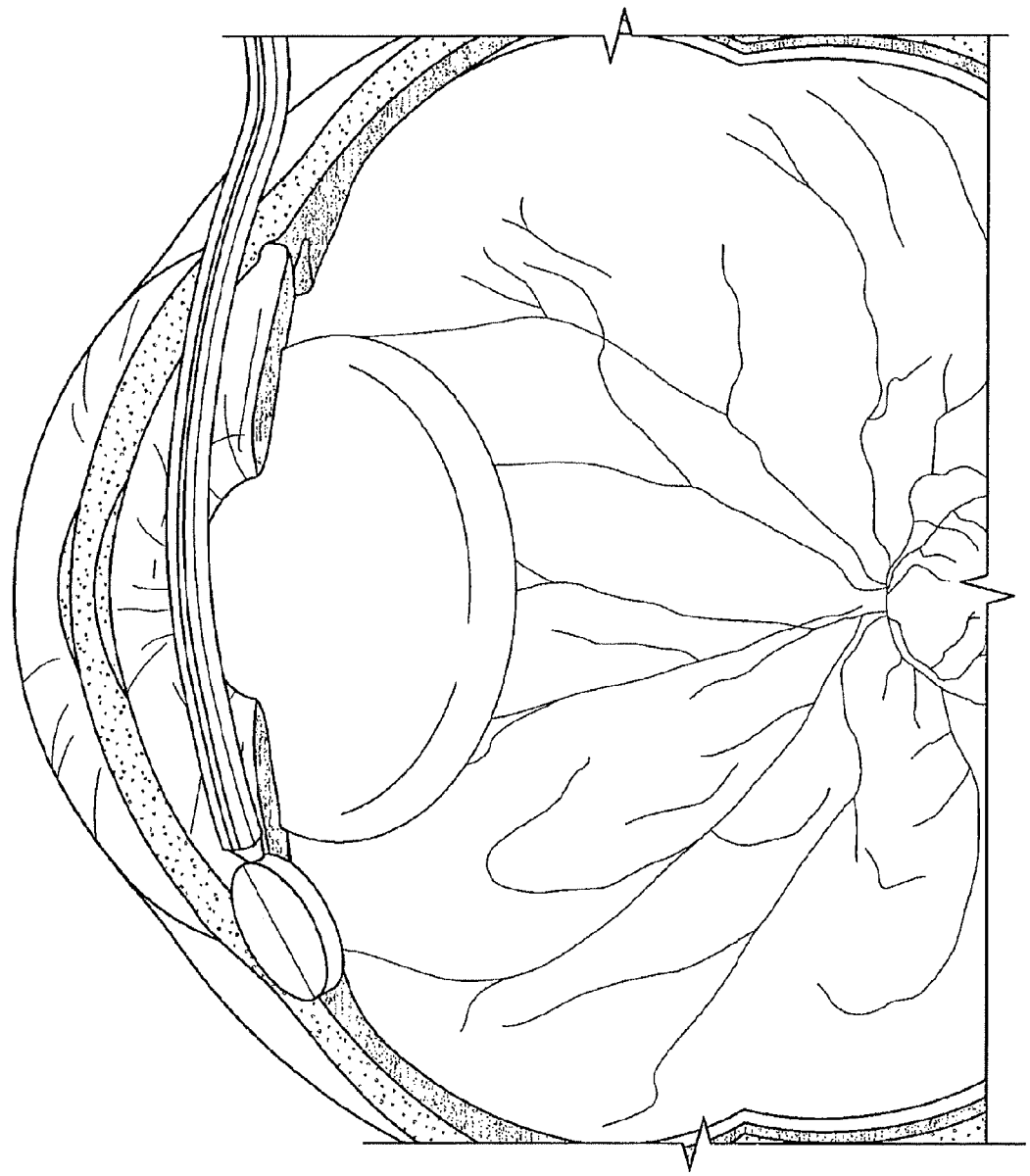
FIG. 2 shows a diagrammatic representation of a side sectional view of an eye showing the unfolded plate portion of the device and a cannula introducing said device across the anterior chamber at 180° to the site of insertion.

Sutures are not required to hold the device in place once surgically introduced into the eye, as the foldable plate is adapted to locate the device on the inner surface of the sclera in a suprachoroidal space formed by cyclodialysis (FIG. 2). Preferably, the plate is of a disc-like shape which matches the curvature of the eye once unfolded. FIG. 2 depicts an unfolded disc (connected tube not shown) after cannula introduction across the anterior chamber (transcameral). Alternatively, any plate-like configuration which locates the device on the inner surface of the sclera in the suprachoroidal space may be used, such as for example a rectangular foldable plate. Preferably the plate diameter is from 0.05 to 6 mm, and preferably the place thickness is from 12.5 µm to 250 µm. The fluid drainage tube of the ocular device is preferably integral with the plate, and is attached at one end to the plate, preferably at the periphery of the plate. Alternatively, the tube may be microwelded or otherwise fixed to the plate. Fabrication techniques well known in production of intraocular foldable lenses are preferably used in this invention. The tube has a hollow lumen, and is preferably of a length from about 1 mm to 4 mm. Preferred diameters of the tubing comprise an outer diameter of 400-1000 µm, and preferably the inner diameter is from 50 to 500 µm.

The diameter of the tube may be selected so as to provide a resistance to aqueous humor flow of predetermined pressure, preferably being a pressure less than 10 mm Hg. This enables the pressure of the aqueous to be regulated in a controlled manner, providing relief from excess ocular pressure associated with glaucoma, with avoidance of hypotony (uncontrolled low pressure). Alternatively, the tube may contain a valve, for example disposed at the end of the tube opening onto the disc so as to regulate ocular pressure at a predetermined level. Preferably, the valve prevents aqueous flow through the tube at a pressure of less than 10 mm Hg. Examples of valves which may be used include a slit valve. The drainage stops altogether if the pressure drops to a predetermined threshold level controlled by the valve.

The flexible foldable nature of the device according to the present invention enables well established techniques used in cataract surgery to be employed in the treatment of glaucoma. The device according to the present invention may be folded into a cannula and introduced for location into the eye.

Intraocular surgery techniques allow a paracentesis (opening onto the anterior chamber from without at the juncture of the cornea and sclera—the limbus) to be performed and the anterior chamber filled with viscoelastic substance. A cyclodialysis instrument is introduced via the paracentesis, with the paracentesis preferably being carried out 180° from the insertion site. A cyclodialysis is carried out, for example by advancing an instrument tip into the angle between the ciliary body and sclera so as to create a cyclodialysis. This is preferably carried out with direct visualisation via gonioscopy lens viewed through an operating microscope. A surgical gonioscopy lens is preferably placed on the cornea while the cyclodialysis is carried out.

The rolled up ocular device is introduced through a cannula, for example using an introducer such as used in cataract surgery or other ocular surgery, from which the device can be detached by pressing a plunger into the introducer when the device has been inserted into the suprachoroidal space created by the cyclodialysis. The tubing of the device is positioned into the interior chamber, and the plate unfolds in the suprachoroidal space to locate the device in the eye. Because of its size, the device cannot fall through the opening through which it was introduced into the suprachoroidal space by the cyclodialysis. The plate therefore keeps the tube in the appropriate position in the anterior chamber allowing controlled aqueous drainage and providing an effective treatment for elevated ocular pressure.

Figure 3:
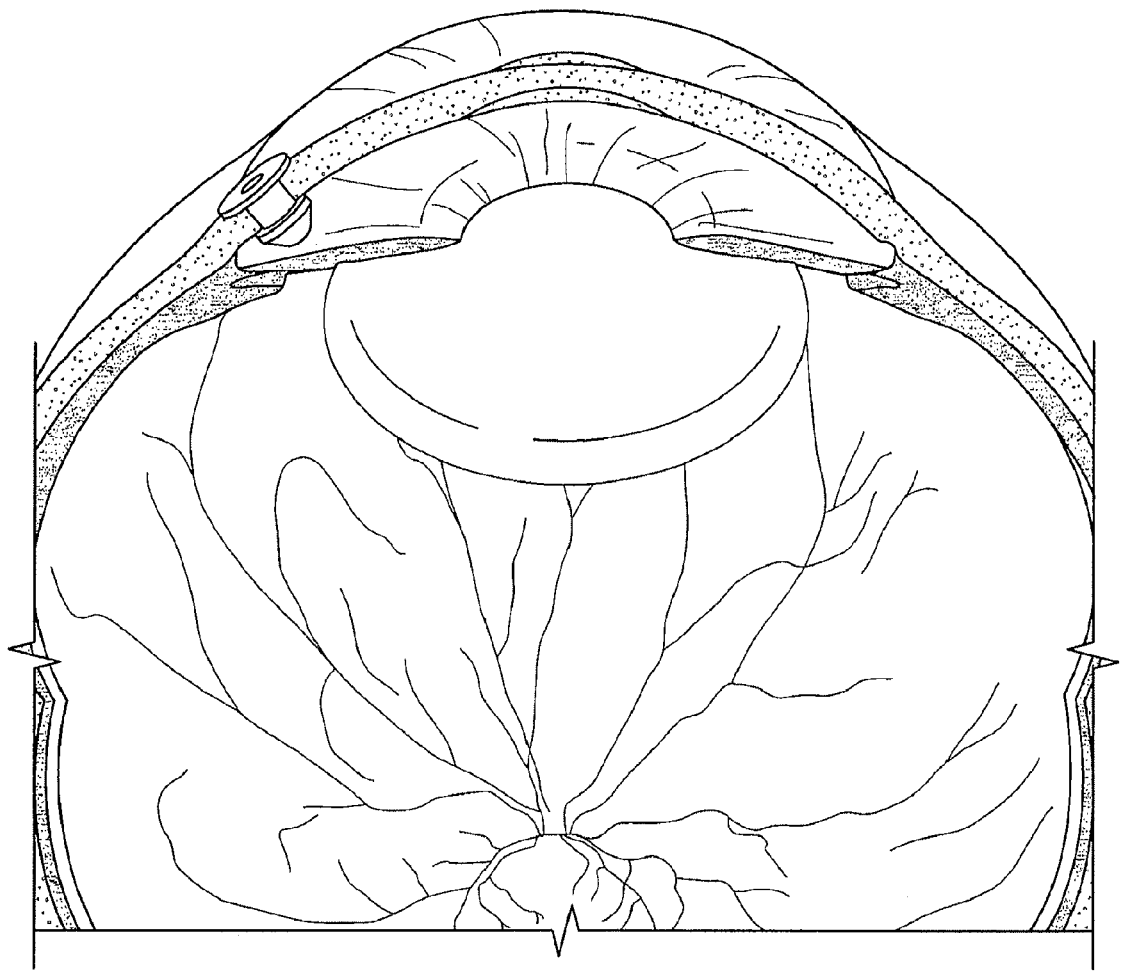
FIG. 3 shows a diagrammatic representation of an eye containing a pressure spike shunt inserted into a paracentesis port.
Figure 4:
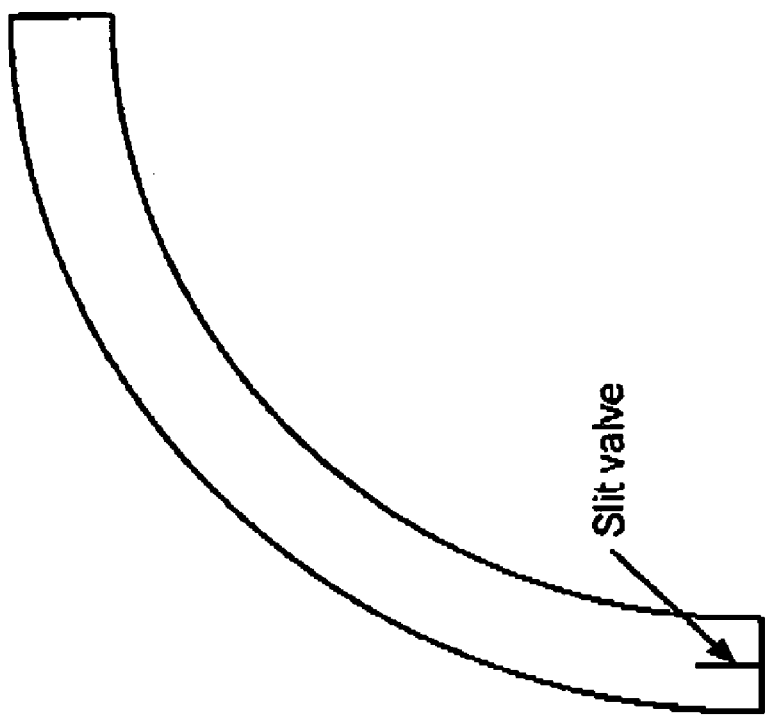
FIG. 4 shows a perspective view of another embodiment of an ocular device described herein.

The pressure spike shunt is designed to fit snugly in a paracentesis port that is routinely made during cataract or other ocular surgery. The tubing will not distort the port and there will be no leakage around the port. The outer end of the tube will sit flush on the surface of the cornea—the inner aspect of the tube will preferably just protrude into the anterior chamber—tube length will generally be 1-2 mm and tube diameter is preferably from 0.4-1.2 mm. The tube will contain the same valvular device as contained in the ocular device described above and will open when the intraocular pressure exceeds a predetermined level, preferably 10 mm Hg. At normal ocular pressure the valve will be closed, closing said tube to any fluid communication. FIG. 3 shows a shunt located in a paracentesis port. In most cases the shunt will be removed and discarded at the first post-operative dressing.

The shunt may be inserted into a paracentesis port, or one or more ports, using. for example, a punctum plug inserting instrument such as described in U.S. Pat. No. 5,741,292.

This invention will now be described with reference to the following examples.

EXAMPLE 1

Fresh whole porcine eyes were taken and mounted in a temperature controlled (37°) perfusion chamber. The eyes were perfused with Balanced Salt Solution via a 30 gauge needle inserted via a paracentesis into the anterior chamber. A peristaltic pump was used at a flow rate of 2 μl/min. Intraocular pressure was continuously monitored via a second paracentesis.

Typically intraocular pressures stabilized at 10-15 mm Hg and fell with time (the "washout effect", as glycosan aminoglycans are washed out of the trabecular meshwork with time). Creation of a cyclodialysis (initially with a small spatula, then viscoelastic injection to enlarge the area of detachment of the ciliary body from the sclera) with or without insertion of the device in the cyclodialysis cleft (silicone tubing, length 3 mm, external diameter—1 mm, plate diameter 3 mm) resulted in lower intraocular pressures (below 10 mm Hg) on reperfusion at the same perfusion rate as control eyes.

EXAMPLE 2

Adequate anesthesia is provided to the eye of a glaucoma patient prepared for intraocular surgery. A paracentesis (opening into anterior chamber from without at the junction of the cornea and sclera—the limbus) is performed and the anterior chamber is filled with a viscoelastic substance. A surgical gonioscopy lens is placed on the cornea (or anterior segment endoscope is used) and a cyclodialysis instrument is introduced via the paracentesis—the paracentesis is carried out 180° away from the planned implant insertion site. The cyclodialysis instrument tip is advanced into the angle and pushed into the space between the ciliary body and sclera creating a cyclodialysis—this is carried out with direct visualization via the gonioscopy lens viewed through an operating microscope. In order to minimize bleeding, the area in the angle (anterior ciliary body face and overlying trabecular meshwork) can be lasered either preoperatively or at the time of surgery to ablate surface blood vessels).

Through an opening at the tip of the cyclodialysis instrument viscoelastic is inserted to further create a space in the suprachoroidal space. The implant is then introduced—the device is rolled up in the same manner as an ultrathin intraocular lens. The ocular device is attached to an introducer from which it is detached by pushing a plunger in the introducer when the implant is inserted into the suprachoroidal space created by the cyclodialysis instrument and viscoelastic. The tubing is then positioned into the anterior chamber and may be cut to size. The plate unfolds in the suprachoroidal space and because of its size cannot fall through the opening through which it was introduced into the suprachoroidal space. The plate therefore keeps the tube in an appropriate position. The valve is then flushed (with a cannula inserted via the paracentesis) via the tube opening in the anterior chamber. Viscoelastic is then removed from the anterior chamber and antibiotics, steroids and a dressing applied to the eye.

EXAMPLE 3

Fresh whole porcine eyes were taken and mounted in a temperature-controlled (37°) perfusion chamber as in Example 1. The eyes were perfused with Balance led Salt Solution via a 30 gauge needle inserted via a paracentesis into the anterior chamber. A peristaltic pump was used at a flow rate of 2 μl/min. Intraocular pressure was continuously monitored via a second paracentesis.

Typically intraocular pressures stabilized at 10-15 mm Hg and fell with time (the "washout effect, as glycoaminoglycans are washed out of the trabecular meshwork with time). Silicone tubing (length 3 mm, external diameter 1 mm) was introduced into one paracentesis port. One end of the port (outer end) was flush with the cornea and the inner end of the port extended slightly into the anterior chamber. Intraocular pressure did not exceed 10 mm Hg.

What is claimed:

1. An ocular implant system for implanting an ocular device into the eye, comprising:
    a fluid drainage device configured to be deployed in the eye so as to locate a first end of the fluid drainage device in communication with the suprachoroidal space, the fluid drainage device having an internal lumen wherein a first end of the lumen of the drainage device communicates with the suprachoroidal space and a second end of the lumen of the drainage device opens into the anterior chamber when implanted in a deployed location in the eye such that the internal lumen provides a fluid passageway from the anterior chamber towards the suprachoroidal space, so as to provide aqueous pressure regulation by draining aqueous humor from the anterior chamber towards the suprachoroidal space via the internal lumen, said fluid drainage device configured to be inserted into the eye through a self-sealing incision in the cornea and wherein the fluid drainage device has a second end configured to be located inside the anterior chamber such that the second end is outside of the ciliary body and posterior of an inner surface of the cornea when in the deployed location; and
    a delivery instrument comprising an elongated member that removably couples to the fluid drainage device, wherein the delivery instrument is configured to introduce the fluid drainage device into the anterior chamber through the corneal incision, advance the fluid drainage device through the anterior chamber, detach at least a portion of the ciliary body from the sclera to form an internal space between the ciliary body and the sclera, advance the implant through the internal space, and detach the fluid drainage device from the elongated member and into the deployed location.

2. The device of claim 1, wherein the device is formed of a biocompatible elastomeric material.

3. The device of claim 1, wherein the device is collapsible to a diameter of 1.5 mm or less.

4. The device of claim 1, wherein the fluid drainage device has an external diameter of 1 mm or less.

5. The device of claim 1, wherein the fluid drainage device has a length of less than 4 mm.

6. The device of claim 1, wherein at least a portion of the device has a curvature that matches the curvature of the eye.

7. An ocular device as in claim 1, wherein the entire device is cylindrical.

8. An ocular device as in claim 1, wherein the fluid drainage device is a tube.

9. An ocular implant system for implanting an ocular device into the eye, comprising:
    a fluid drainage device configured to be deployed in the eye so as to locate a first end of the fluid drainage device in communication with the suprachoroidal space, the fluid drainage device having an internal lumen wherein a first end of the lumen of the drainage device communicates with the suprachoroidal space and a second end of the lumen of the drainage device opens into the anterior chamber when implanted in a deployed location in the eye such that the internal lumen provides a fluid passageway from the anterior chamber towards the suprachoroidal space, so as to provide aqueous pressure regulation by draining aqueous humor from the anterior chamber towards the suprachoroidal space via the internal lumen, wherein the fluid drainage device has a second end configured to be located inside the anterior chamber such that the second end is outside of the ciliary body and posterior of an inner surface of the cornea when the device is in the deployed location, wherein the device is configured to be implanted into the eye through an incision in the cornea; and a delivery instrument comprising an elongated member that removably couples to the fluid drainage device, wherein the delivery instrument is configured to introduce the fluid drainage device into the anterior chamber through the corneal incision, advance the fluid drainage device through the anterior chamber, detach at least a portion of the ciliary body from the sclera to form an internal space between the ciliary body and the sclera, advance the implant through the internal space, and detach the fluid drainage device from the elongated member and into the deployed location.

10. The device of claim 9, wherein the device is formed of a biocompatible elastomeric material.

11. The device of claim 9, wherein the device is foldable to a diameter of 1.5 mm or less.

12. The device of claim 9, wherein the fluid drainage device has an external diameter of 1 mm or less.

13. The device of claim 9, wherein the fluid drainage device has a length of less than 4 mm.

14. An ocular device as in claim 9, wherein the entire device is cylindrical.

15. An ocular device as in claim 9, wherein the fluid drainage device is a tube.

16. An ocular implant system for implanting an ocular device into the eye, comprising:

a fluid drainage device configured to be deployed in the eye so as to locate a first end of the fluid drainage device in communication with the suprachoroidal space, the fluid drainage device having an internal lumen wherein a first end of the lumen of the drainage device communicates with the suprachoroidal space and a second end of the lumen of the drainage device opens into the anterior chamber when implanted in a deployed location in the eye such that the internal lumen provides a fluid passageway from the anterior chamber towards the suprachoroidal space, so as to provide aqueous pressure regulation by draining aqueous humor from the anterior chamber towards the suprachoroidal space via the internal lumen, wherein the fluid drainage device has a second end configured to be located inside the anterior chamber such that the second end is outside of the ciliary body and posterior of an inner surface of the cornea, wherein the device is configured to be implanted into the eye through an incision in the cornea; and a delivery instrument comprising an elongated member that removably couples to the fluid drainage device, wherein the delivery instrument is configured to introduce the fluid drainage device into the anterior chamber through the corneal incision, advance the fluid drainage device through the anterior chamber, detach at least a portion of the ciliary body from the sclera to form an internal space between the ciliary body and the sclera, advance the implant through the internal space, and detach the fluid drainage device from the elongated member and into the deployed location.

17. The device of claim 16, wherein the device is formed of a biocompatible elastomeric material.

18. The device of claim 16, wherein the device is foldable to a diameter of 1.5 mm or less.

19. The device of claim 16, wherein the fluid drainage device has an external diameter of 1 mm or less.

20. The device of claim 16, wherein the fluid drainage device has a length of less than 4 mm.

21. The device of claim 16, wherein sutures are not required to hold the device in the eye.

22. The device of claim 16, wherein the device is manufactured of a material that is sufficiently soft so as to not erode choroid material when inserted into the eye.

23. An ocular device as in claim 16, wherein the entire device is cylindrical.

24. An ocular device as in claim 16, wherein the fluid drainage device is a tube.

25. An ocular implant system for implanting an ocular device into the eye, comprising:

a fluid drainage device configured to be implanted in a deployed location in the eye via an incision in the cornea so that a first end of the fluid drainage device is positioned in the anterior chamber of the eye and a second end of the fluid drainage device is positioned in communication with the suprachoroidal space of the eye, the fluid drainage device having an internal lumen wherein a first opening at a first end of the internal lumen of the drainage device opens into the anterior chamber and a second opening at a second end of the internal lumen of the drainage device communicates with the suprachoroidal space when in the deployed location such that the internal lumen provides a direct fluid passageway from the anterior chamber towards the suprachoroidal space for aqueous pressure regulation when implanted in the deployed location in the eye and wherein the first end of the fluid drainage device is configured to be located inside the anterior chamber such that the first end is outside of the ciliary body and posterior of an inner surface of the cornea; and a delivery instrument comprising an elongated member that removably couples to the fluid drainage device, wherein the delivery instrument is configured to introduce the fluid drainage device into the anterior chamber through the corneal incision, advance the fluid drainage device through the anterior chamber, detach at least a portion of the ciliary body from the sclera to form an internal space between the ciliary body and the sclera, advance the implant through the internal space, and detach the fluid drainage device from the elongated member and into the deployed location.

26. An ocular device as in claim 25, wherein sutures are not required to hold the device in the eye.

27. An ocular device as in claim 25, wherein the fluid drainage device is cylindrical.

28. An ocular device as in claim 25, wherein the fluid drainage device has a length of 3 mm or more.

29. An ocular device as in claim 25, wherein the fluid drainage device has a length of about 3-4 mm.

30. An ocular device as in claim 25, wherein the fluid drainage device is positioned entirely within the interior of the eye radially inward of an outer globular boundary defined by an outer surface of the sclera when in the deployed location.

31. An ocular device as in claim 25, wherein the entire device is cylindrical.

32. An ocular device as in claim 25, wherein the fluid drainage device is a tube.

33. An ocular implant system, comprising:

an ocular implant comprising an elongated body having a proximal end region, a distal end region, and an internal lumen communicating with an inlet port in the proximal end region and an outlet port in the distal end region, the ocular implant configured to be introduced into the anterior chamber of the eye via an incision in the cornea and positioned in a deployed location wherein the inlet port is in the anterior chamber of the eye and the outlet port is in communication with the suprachoroidal space and at least a portion of implant is in contact with an inner surface of sclera of the eye so that the internal lumen provides a fluid passageway from the anterior chamber towards the suprachoroidal space; and a delivery instrument comprising an elongated member that removably couples to the ocular implant, wherein the delivery instrument is configured to introduce the ocular implant into the anterior chamber through the corneal incision, advance the ocular implant through the anterior chamber, detach at least a portion of the ciliary body from the sclera to form an internal space between the ciliary body and the sclera, advance the implant through the internal space, and detach the ocular implant from the elongated member and into the deployed location.

34. A system as in claim 33, wherein the ocular implant is a tube.

35. A system as in claim 33, wherein the ocular implant is cylindrical.

36. A system as in claim 33, wherein the elongated member of the delivery instrument is a cannula.

37. A system as in claim 33, wherein the delivery instrument is configured to introduce the ocular implant into the anterior chamber through a self-sealing corneal incision.

38. A system as in claim 33, wherein the elongated member of the delivery instrument is sized to deliver the implant across the anterior chamber to a delivery site positioned 180 degrees from the incision.

* * * * *